United States Patent [19]

Friedman et al.

[11] Patent Number: 4,699,589
[45] Date of Patent: Oct. 13, 1987

[54] APPARATUS AND METHOD FOR SUPPLYING A HEATED LIQUID

[75] Inventors: Aaron Friedman, Wethersfield; H. Gordon Minns, Suffield, both of Conn.

[73] Assignee: National Patent Dental Products, Inc., New Brunswick, N.J.

[21] Appl. No.: 827,793

[22] Filed: Feb. 7, 1986

[51] Int. Cl.⁴ .............................................. A61G 17/02
[52] U.S. Cl. ........................................ 433/80; 433/32; 128/66
[58] Field of Search .............. 433/32, 80, 84; 128/66, 128/62 A

[56] References Cited

U.S. PATENT DOCUMENTS

| | | | |
|---|---|---|---|
| 3,044,465 | 7/1962 | Anderson et al. | 128/62 A |
| 3,227,158 | 1/1966 | Mattingly | 128/66 |
| 3,420,228 | 1/1969 | Kalbfeld | 128/66 |
| 3,776,825 | 12/1973 | Vit | 204/81 |
| 3,863,628 | 2/1975 | Vit | 128/66 |
| 3,886,266 | 5/1975 | Goldman et al. | 424/53 |
| 3,932,605 | 1/1976 | Vit | 424/51 |
| 3,943,628 | 3/1976 | Kronman et al. | 433/89 |
| 4,012,842 | 3/1977 | Vit | 433/216 |
| 4,184,064 | 1/1980 | Williams | 433/32 |
| 4,249,899 | 2/1981 | Davis | 433/32 |
| 4,302,186 | 11/1981 | Cammack et al. | 433/80 |

Primary Examiner—Robert P. Swiatek
Assistant Examiner—Andriene J. Lepiane
Attorney, Agent, or Firm—Vincent P. Pirri

[57] ABSTRACT

An improved method and apparatus for effecting delivery of a chemical solution useful in the softening of tooth caries and/or plaque in a patient's mouth utilizes a reciprocating piston-type pump having flow and pressure regulation for injecting a pulsating jet stream of the solution at a controlled rate and pressure, in combination with a separate heater device adjacent an applicator maintaining the temperature of the solution at or near body temperature as it is delivered to the mouth.

7 Claims, 13 Drawing Figures

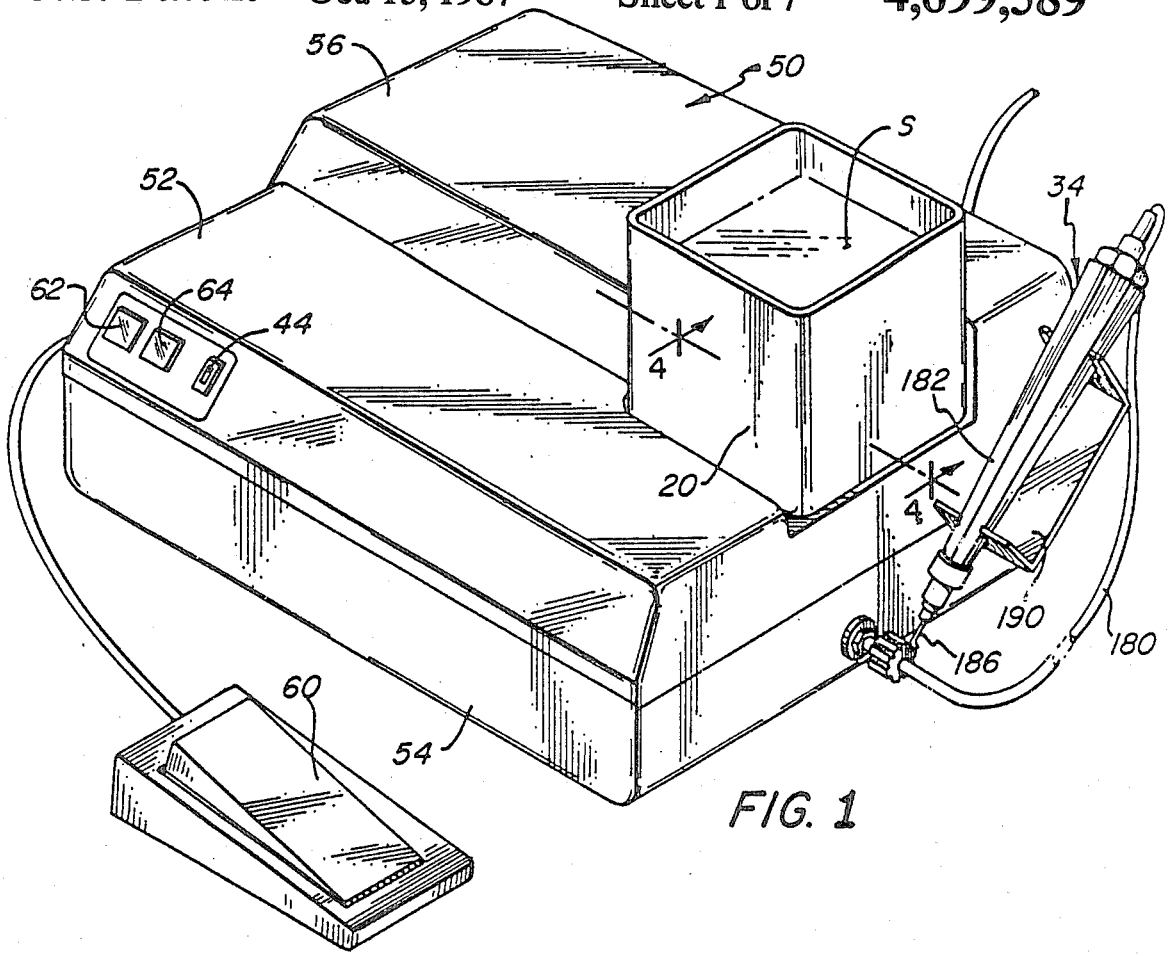
FIG. 1
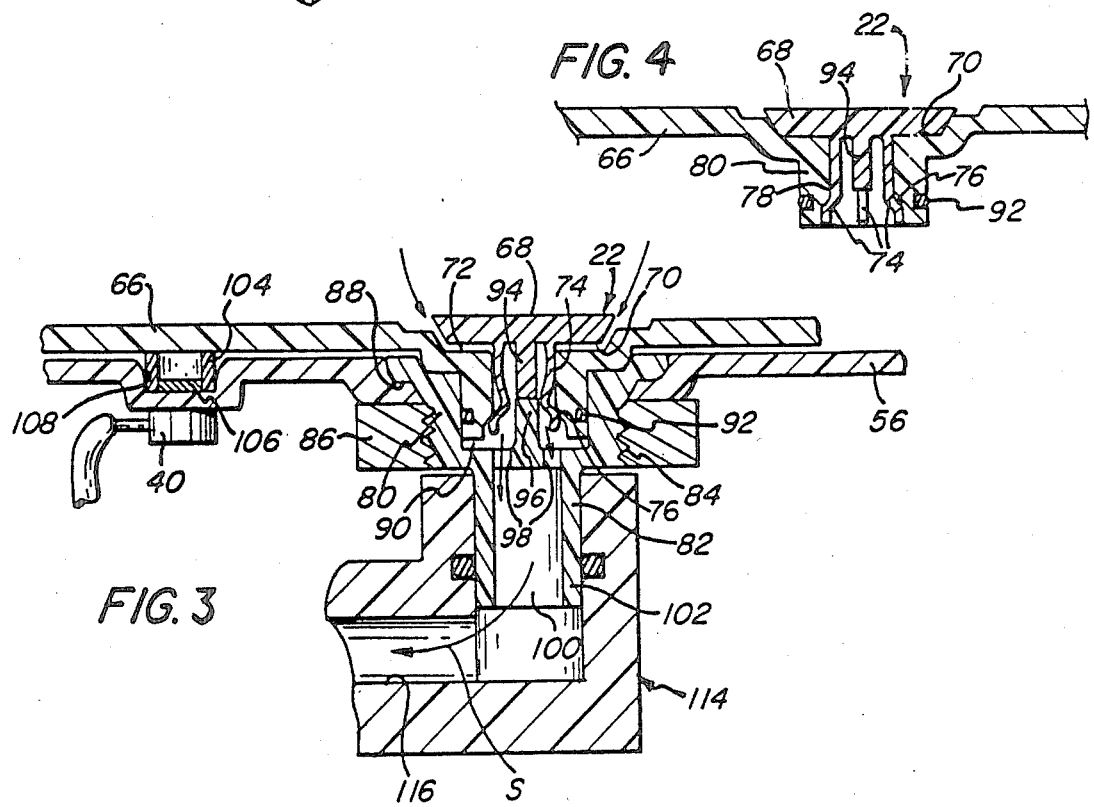
FIG. 4
FIG. 3

APPARATUS AND METHOD FOR SUPPLYING A HEATED LIQUID

BACKGROUND OF THE INVENTION

This invention relates to an apparatus for supplying a liquid heated to a predetermined temperature. In particular, the invention relates to an apparatus for intermittently supplying a dental treating solution to the oral cavity of a patient with the solution being heated to about the normal body temperature of the patient, and to a method of treating employing such apparatus.

A common method for removing carious lesions in teeth is through the use of power operated tools in conjunction with hand manipulated tools. Thus, complete removal of carious material by the dentist requires the use of rotary cutting instruments as well as hand instruments. Such dental procedures impart a high degree of apprehension and fear to many dental patients, particularly children. Other dental patients have problems and/or reactions with local anesthetic injection which are oftentimes given in those instances where the carious lesions are fairly extensive and deep.

Within the past decade, methods have been developed which utilize certain chemical solutions to soften and remove dental caries. Such methods substantially reduce and even eliminate the need for mechanical removal of the carious lesion by the use of drills and burrs. Suitable solutions can be prepared by forming an admixture containing (a) at least one aminoalkanoic acid containing from 1 to about 18 carbon atoms, e.g., DL-2-aminobutryic acid, glycine, etc., (b) an alkali metal hydroxide, e.g., sodium hydroxide, (c) an alkali metal halide, e.g., sodium chloride, and (d) an alkali metal hypochlorite, e.g., sodium hypochlorite, in deionized water and preferably maintained at a pH of from about 9 to about 12. The active ingredient is believed to be N-chlorinated aminoalkanoic acid(s) and/or the alkali metal salt(s) thereof. A preferred formulation is (a) DL-2-aminobutyric acid and/or glycine, (b) sodium hydroxide, (c) sodium chloride and (d) sodium hypochlorite. The molar ratios of components (a), (b) and (c) can vary advantageously are about 1:1:1 with the molar ratio of component (a) relative to component (d) exceeding 1, e.g., about 5 to 10, in one liter of deionized water. The active ingredient presumably reacts with the decalcified, partially degraded collagen of the carious lesion resulting in a softening of the carious material. For information on this subject, reference is made to U.S. Pat. Nos. 3,886,266; 3,932,605; 3,991,107; 4,012,842; and 3,776,825, the subject matter of which is incorporated herein by reference. The aforesaid caries removal solution has a relatively short half life and should be prepared just prior to use.

A delivery system for administering the caries removal solution to the carious lesion is disclosed in U.S. Pat. Nos. 3,776,825 and 3,943,628 and can consist of a reservoir for the solution, a pump having an inlet connected to the reservoir and a handpiece with a uniquely designed applicator tip connected to the outlet side of the pump. The solution is delivered in a fine pulsing stream through the handpiece to the carious site where it softens the decayed material. The dentist can then remove the softened carious material by light abrasion with the applicator tip while flushing with the solution. Prior attempts to employ a caries removal device or system which comprises solely an applicator, a source or reservoir of the chemical solution and pump means connected between the applicator and the chemical solution source for periodically delivering the chemical solution under pressure to the applicator have not proven particularly successful.

Desirably, the temperature of the caries removal solution at the time of application to the carious lesion should be maintained within a range that affords maximum comfort to the dental patient, e.g., from about 90° F. to about 105° F., which covers the range of normal body temperature of the patient. A temperature significant beyond this range can cause discomfort and may traumatize the patient.

The chemical solution is desirably applied to the carious lesion as a soothing, pulsating stream through a tube connected to the applicator tip at an optimum flow rate of about 35±5 ml/minute. The pulsation frequency of the stream is desirably maintained in the range of about 1000 to 1600 cycles/minute while its pressure is advantageously varied from about 10 to about 15 psi (per pulsation cycle). The flow rate, pulsation rate and pressure of the stream should be selected so as to balance facility of application of the stream to the caries site with due regard for the patient's comfort.

In order to achieve these objectives, the chemical solution must be heated from an ambient state when placed in the reservoir to approximately 98.6°F., or normal body temperature. Thus, it has been suggested in U.S. Pat. Nos. 3,863,628 and 4,012,842 to employ a heater as a part of the pump to bring the chemical solution to body temperature as it is pumped to the applicator. The heater includes a heating element embedded in a conductive block forming one side wall of the pump chamber. The block is disposed opposite to, and spaced from, a flexible diaphragm which is reciprocated so that chemical solution from a reservoir is received in the chamber between the diaphragm and heater block and forced by the diaphragm out of the chamber to a hand-held applicator during reciprocation of the diaphragm by a cam mechanism connected to a drive motor. This arrangement proves impractical in that the diaphragm cannot withstand the required frequency of operation cycle and fails after a relatively brief period of service.

Further, while the dwell time of the cam mechanism between the diaphragm and drive motor can be adjusted to increase or decrease the relaxation, or inactive, period of the pump to cause a pulsating drive of the chemical solution, there are no means to regulate the flow rate or pressure of application of the chemical solution, which, if too high, can cause harm to the patient by tearing of gum tissue adjacent the treated teeth.

Thus, the need for an improved chemical solution delivery system for applying the solution to a tooth with carious lesion in a pressure and flow-controlled, properly heated state, is desirable.

It has long been known that reciprocating, piston-type pumps can be used to deliver a pulsating stream or jet of water to teeth for oral hygiene such as cleansing, massaging and stimulating gum tissue. Examples of such pump constructions are shown in U.S. Pat. Nos. 3,227,158 and 3,420,228, the former illustrating the pump forming the basis of the well-known WATER-PIK system. Such pumps do not exhibit the objectionable wear characteristics typical of a bellows or flexed diaphragm-type active pump element and through the introduction of suitable valving adjacent the inlet and outlet of the pump chamber, flow and pressure control of the pumped fluid may be obtained.

The disadvantages associated with known types of heated liquid delivery systems are not confined to the aforementioned diaphragm-type pumping mechanisms. The heater devices which have been incorporated into these systems are inadequate to the task for reasons which are inherent in their design.

In a known type of heater device, a liquid to be heated is circulated about, or otherwise brought into direct contact with, an electrically powered insulated heating element with heat being transferred from the heating element to the liquid. The heater device is associated with suitable control means for heating the liquid at or within a few degrees of a predetermined temperature. The device operates well when there is a sufficient flow of liquid past the heating element to continuously carry away heat therefrom. However, when the delivery of electrical power to the heating element is temporarily interrupted, e.g., when the flow of liquid is discontinued, residual heat from the heating element continues to transfer to the liquid in the vicinity of the heating element causing the liquid to overheat. In fact, overheating can occur to such an extent that the liquid in proximity to the heating element begins to boil. Such a heater device is therefore entirely unacceptable for heating liquids to be contacted with, or introduced into, the body. Such a device poses the additional disadvantage that in the case of a corrosive liquid, there is a danger that the liquid will eventually penetrate the casing of the heating element thereby coming into electrical contact with the liquid. The hazard of an accidental electrocution in such circumstances is in itself sufficient reason to preclude the use of such a heater device in apparatus intended to supply a heated body-treating liquid.

SUMMARY OF THE INVENTION

It is an object of the invention to provide a heated liquid delivery system having an improved pump device.

It is a further object of the invention to provide a heated liquid delivery system having an improved liquid heating device, with or without combination with the aforementioned improved pump device.

It is a particular object of the invention to provide an improved apparatus for intermittently supplying a dental treating solution to the oral cavity of a patient with the solution being heated to about the normal body temperature of the patient.

In keeping with the foregoing objects there is provided a heated liquid delivery apparatus comprising:
 (a) a pump for delivering liquid to a heater device, said pump comprising a reciprocating piston-type pump; and
 (b) an electrically powered, intermittently operated heater device for heating the liquid discharged from said pump to a predetermined temperature.

Further in keeping with the present invention, there is provided a heated liquid delivery apparatus comprising:
 (a) a pump for delivering liquid to a heater device; and,
 (b) an electrically powered, intermittently operated heater device for heating the liquid discharged from the pump to a predetermined temperature, said heater device comprising:
  (i) a heat sink;
  (ii) an electrical resistance heating element embedded within the heat sink such that when electrical power is delivered to the heating element, heat is transferred therefrom to the heat sink and when the delivery of electrical power to the heating element is temporarily interrupted, residual heat in the heating element is transferred therefrom to the heat sink, the total quantity of heat transferred to the heat from the heating element not exceeding the heat capacity of the heat sink so that the temperature of the heat sink remains relatively constant both when electrical power is being delivered to the heating element and when the delivery of electrical power to the heating element is temporarily interrupted; and,
  (iii) a conduit for the flow of a liquid to be heated to a predetermined temperature substantially corresponding to the temperature of the heat sink, the conduit having an inlet for admitting liquid at a temperature below the predetermined temperature and an outlet for discharging liquid at the predetermined temperature, the conduit being embedded within the heat sink such that heat is transferred from the heat sink to liquid present in the conduit raising the temperature of the liquid from the temperature at the conduit inlet to the predetermined temperature at the conduit outlet.

In a preferred embodiment of the heating liquid delivery system of this invention, both the improved pump and improved heater device are combined in the same unit with the unit benefiting from the advantages of both components.

The reciprocating piston-type pump has been found to withstand the rigors of the type of service to which the liquid delivery system is apt to be put, in particular, the dental treating procedures hereinafter more fully described. Unlike the diaphragm or bellows-type pumps of the known devices, a reciprocating piston-type pump is capable of providing fairly maintenance-free service for several hundred hours of operation compared to perhaps 40 hours or even less for the former type pump mechanisms.

The heater device of this invention completely overcomes the disadvantages associated with the known type of heater device described above. Thus, the ability of the heat sink component of the heater device herein to continue to absorb residual heat from the heating element when the delivery of power to the heating element has been temporarily interrupted prevents the temperature of the heat sink from exceeding the range of temperature to which it is desired to heat the liquid present in the conduit by any significant extent. In addition, since there is no direct contact of the heating element with the conduit in the device of this invention, there is little, if any, opportunity for the liquid present in the conduit to even come into electrical contact with the heating element.

BRIEF DESCRIPTION OF THE DRAWINGS

Further objects and advantages of the invention will become apparent from the following description and claims, and from the accompanying drawings, wherein:

FIG. 1 is a perspective view of one embodiment of an apparatus in accordance with this invention especially adapted for supplying a heated caries/plaque removal solution to the oral cavity of a patient undergoing treatment;

FIG. 3 is a cross-sectional view taken substantially along the plane indicated by line 4—4 of FIG. 1;

FIG. 4 is an enlarged cross-sectional view of the check valve portion of the apparatus of FIG. 3;

DESCRIPTION OF THE PREFERRED EMBODIMENTS

Figure 2:
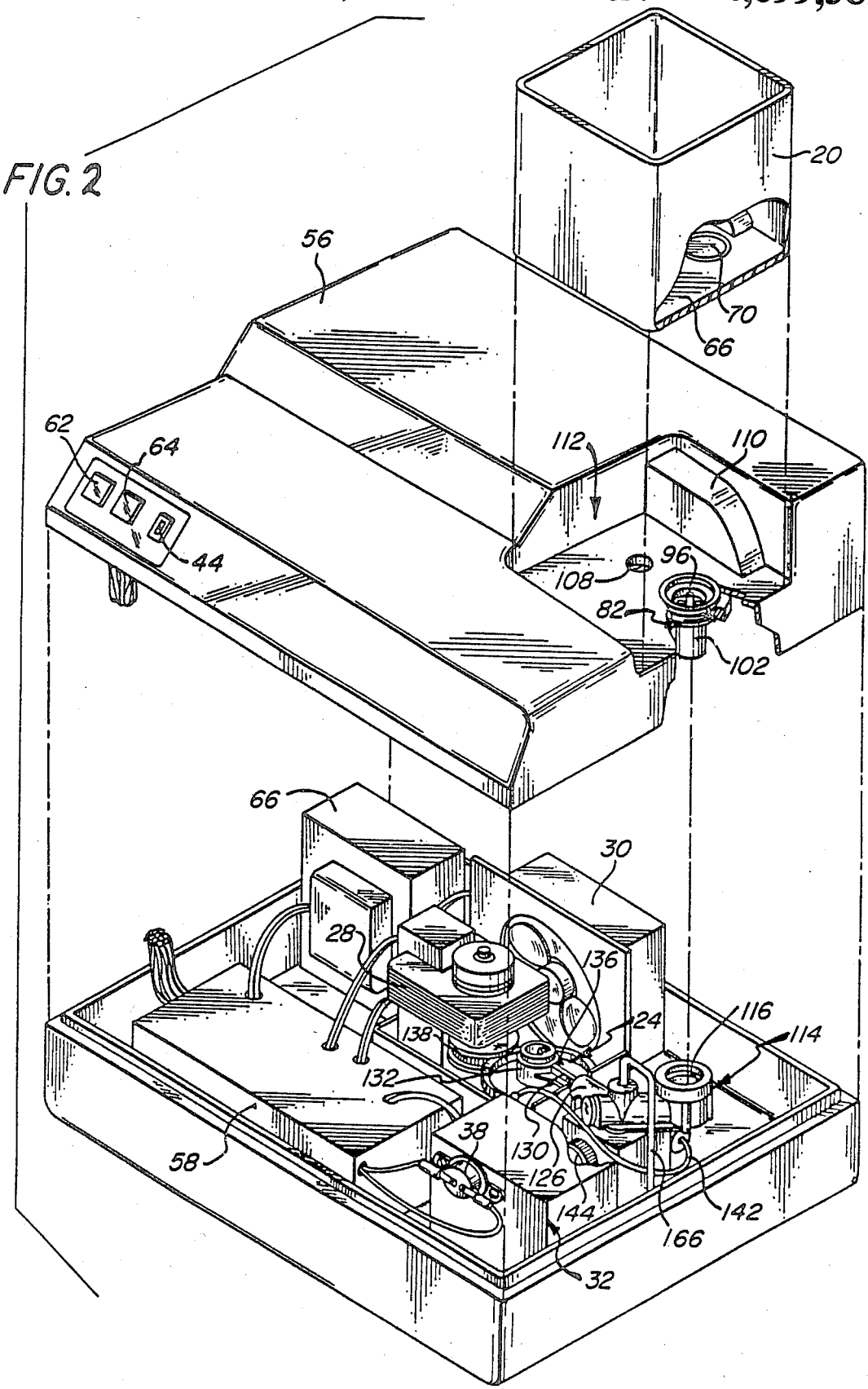
FIG. 2 is an exploded perspective view of the apparatus of FIG. 1.
Figure 13:
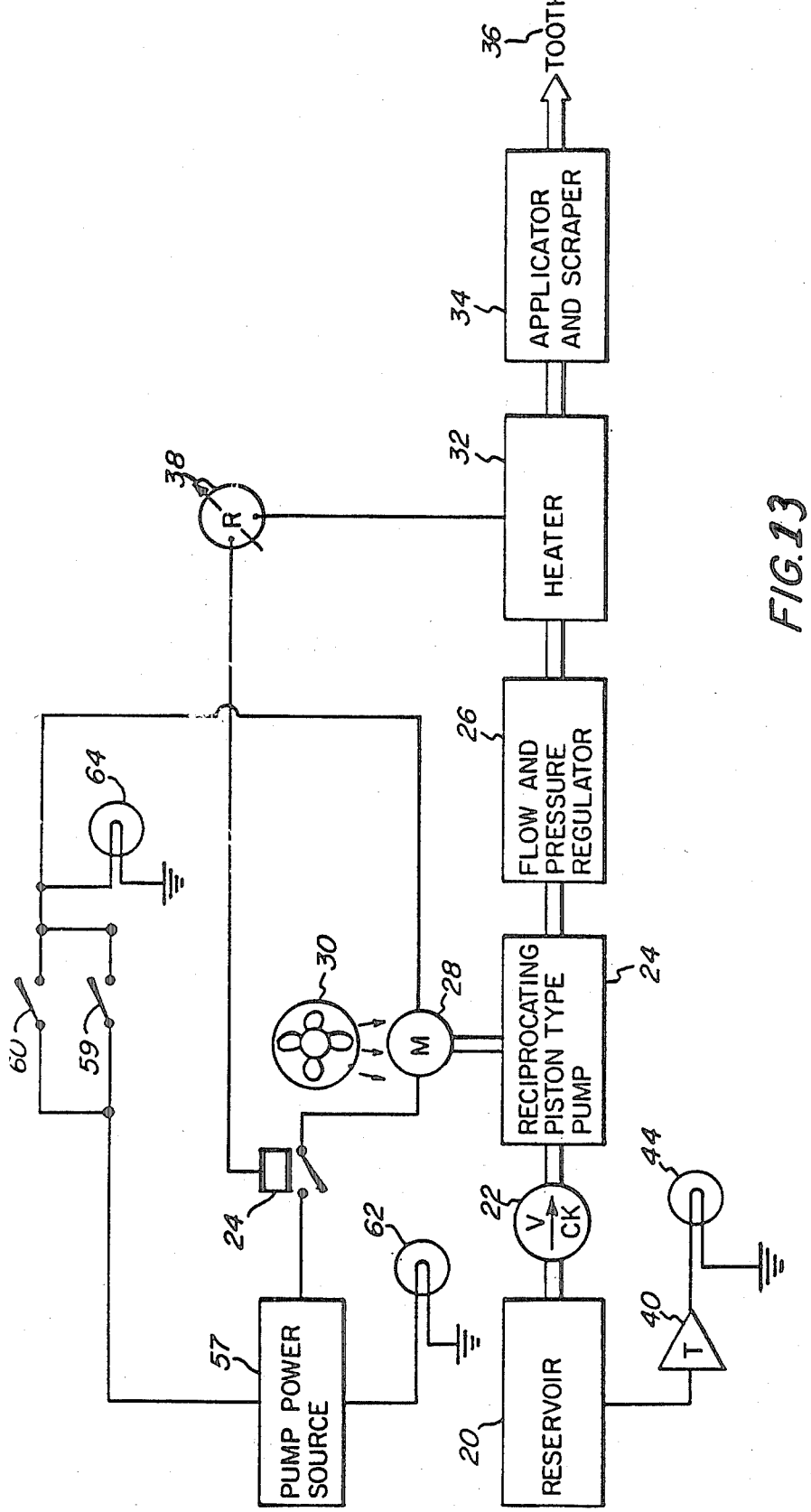

Referring now to the drawings in detail, wherein like numerals indicate like elements throughout the several views, FIGS. 1 and 2 illustrate the overall assembly of an apparatus 50 the components and use of which are diagrammatically illustrated in FIG. 13. A two-piece case 52 consisting of a box 54 and cover element 56 is adapted to house motor 28, a reciprocating piston-type pump 24, heater device 32 and fan 30 used to cool the motor. Suitable circuitry of known and conventional design is housed at 58 to effect a variety of control functions such as regulating the operation of electric motor 28 and controlling the intermittent delivery and interruption of power to heater device 32. Timer element 40 is also mounted beneath cover element 56 and is connected via suitable circuitry at 58 to visual indicator lamp 44 on cover element 56 which will be illuminated in a flashing or interrupted pattern after a given predetermined time interval once a reservoir 20 containing a quantity of a caries removal liquid, designated Solution S, is seated on the cover element 56.

In addition to a general power on/off switch (not shown), a hand-operated control 59 (FIG. 13) or, alternatively, a foot pedal 60, can be provided to intermittently activate the motor and pump assembly, and therefore, regulate the flow of Solution S as required. In either event, a suitable visual display 62 can be provided to indicate when power to the entire unit is on and a second visual display 64 can be provided to indicate when the hand-operated control or foot pedal has activated the motor/pump assembly.

An isolation transformer 65 can also be placed in the circuit between the power source and the various electrical components of apparatus 50 to preclude electrical shock to anyone touching case 52.

The source of caries removal Solution S can be maintained in two separate reservoirs and admixed just prior to application. Measured amounts of particular components of the solution, as discussed heretofore, can be withdrawn from the two reservoirs, mixed in a small mixing chamber to form the active caries removal solution and withdrawn from one reservoir, such as reservoir 20 shown herein, through a check valve and pumped through a heater and thereafter applied to the carious site in fine pulsating stream through applicator 34. A suitable formulation for Solution S is as follows:

| | |
|---|---|
| DL-2-aminobutyric acid and/or Glycine | 0.04–0.06 Mol |
| Sodium Hydroxide | 0.04–0.06 Mol |
| Sodium Chloride | 0.04–0.06 Mol |
| Sodium Hypochlorite | 0.005–0.01 Mol |
| Deionized Water | An amount sufficient to make one liter of solution |
| pH of solution | approx. 10–12 at 20° C. |

As illustrated in FIGS. 2 to 4, inclusive, the bottom wall 66 of reservoir 20 is provided with a pop-up check valve generally designated by the numeral 22. The valve 22 includes a substantially planar disk 68 adapted for mating seated engagement on an annular shoulder 70 of a depression 72 formed in bottom wall 66 of reservoir 20. A plurality of spring fingers 74 extend downwardly from the bottom surface of disk 68 and are adapted to snap over an annular shoulder 76 of a flared portion of a bore 78 on the interior surface of a downwardly extending cylindrical extension 80 of bottom wall 66 of reservoir 20.

The exterior surface of cylindrical extension 80 is received in a fitting 82 having an exterior threaded portion 84 adapted to receive nut 86 to clamp the fitting 82 in an annular countersunk bore 88 in cover 52. Extension 80 is received within central bore 90 of fitting 82 when the reservoir 20 is mounted on cover 52 and an annular O-ring seal 92 on the exterior of cylindrical extension 80 forms a fluid impervious connection between the fitting 82 and cylindrical extension 80.

When the cylindrical extension 80 (as shown in FIG. 3) on the bottom wall 66 of reservoir 20 is inserted in the bore 90 of fitting 82 after the reservoir has been filled with caries removal solution, a downwardly depending central stem 94 on disk 70 strikes an upwardly extending central stem 96 in bore 90 of fitting 82 to cause the disk 68 to be raised relative to annular shoulder or seat 72. Spring retaining fingers 74 exert sufficient force against annular shoulder 76 so as to retain disk 70 of check valve 22 in bore 78 albeit raised from shoulder 72.

In the raised position of disk 70, Solution S can be drained from reservoir 20 between disk 70 and annular shoulder 72 into bore 78, bore 90 of fitting 82, and out through a series of openings 98 provided in a circular wall in the bottom of conduit fitting 82 into the bore 100 of a cylindrical drain conduit 102 integral with the bottom of fitting 82. Solution S flows from drain conduit 102 through the inlet of pump 24 as will be made clear hereinafter.

Simultaneously with the insertion of cylindrical extension 80 into bore 90 of fitting 82, a second, downwardly extending cylindrical member 104 on the bottom wall 66 of reservoir 20 having a permanent magnet 106 fixed within the interior thereof is received within a depression 108 on case cover 56. Mounted directly beneath depression 108 is timer 40 which senses the presence of magnet 106 to generate a current through the well-known "Hall effect" to activate the timer delay circuitry which ultimately results in a visual display at lamp 44 after a predetermined time interval to signal that the potency of Solution S has become impaired. At this time, reservoir 20 can be removed from its seat 110 in depression 112 on case cover 56 to change and/or replenish the reservoir with a fresh quantity of Solution S.

Upon removal of reservoir 20 and extension 80 from fitting bore 90, the weight of the remaining Solution S in reservoir 20 will cause disk 68 to slide downwardly to seat against annular shoulder 72 or, if the reservoir is empty, finger pressure may be used to slide the disk downwardly to reseat it on shoulder 72. Spring fingers 74 snap over annular shoulder 76 to maintain check valve 22 closed until reservoir 20 is again filled and reseated on cover 56.

Figure 5:
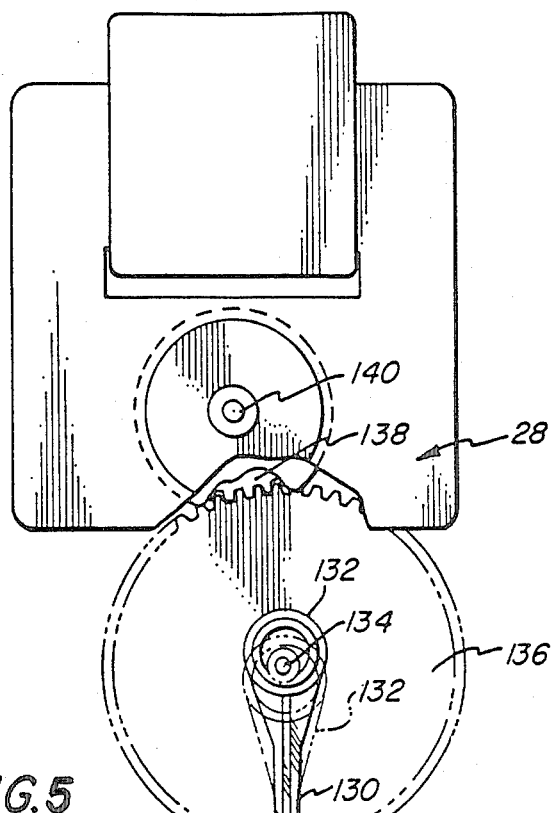
FIG. 5 is a top plan view of the pump assembly of the apparatus of FIGS. 1 and 2, with a portion broken away and illustrated in section for purposes of clarity in describing the operation thereof.
Figure 6:
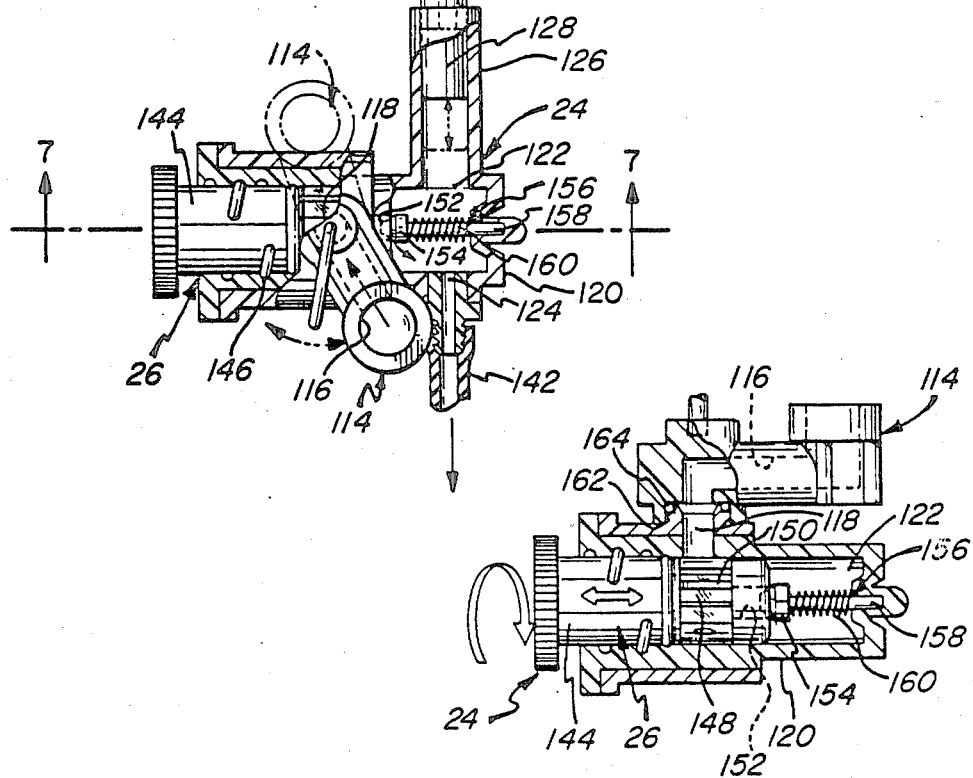
FIG. 6 is a cross-sectional view taken substantially along the plane indicated by line 7—7 of FIG. 5 illustrating the flow and pressure regulator of the pump assembly.

Drain conduit 102 of fitting 82 is received in an L-shaped elbow 114 having an interior conduit 116 for connecting the bore 100 of drain conduit 102 with the inlet port 118 of a reciprocating piston-type pump generally designated by numeral 24 and illustrated in detail in FIGS. 5 and 6.

Pump 24 includes a housing 120 having an inlet port 118 leading to an interior fluid receiving chamber 122, an outlet port 124 and a cylinder extension 126 receiving the plunger 128 of a reciprocable piston 130 opposite to, but adjacent, outlet port 124.

Piston 130 is secured to an eccentrically mounted cam 132 fixed to a shaft 134 extending upwardly from the center of a rotatable gear 136 in mesh with a pinion 138 connected to output drive shaft 140 of electric motor 28. Upon activation of motor 28, pinion 138 will rotate gear 136 and shaft 134. Rotation of shaft 134 will cause eccentric cam 132 to travel about shaft 134 causing piston 130 to reciprocate in cylinder extension 126. Reciprocation of piston 130 in cylinder extension 126 will cause plunger 128 to force fluid in chamber 122 out outlet port 124 through tubing 142 to heater device 32.

The flow and pressure of liquid or Solution S exiting outlet 124 of pump 24 can be regulated by flow and pressure regulator 26. This flow and pressure regulator includes a rotatable hollow valve body 144 threadedly received at 146 in the interior of housing 120. The end of valve body 144 within housing 120 includes a plurality of baffles 148 separated by openings 150 through which Solution S can flow from inlet port 118 into the hollow interior of valve body 144. Solution S can exit from the interior of valve body 144 through a cylindrical bore 152 into the interior of fluid receiving chamber 122 opposite piston plunger 128 adjacent outlet port 124 of pump 24. Seated in the end of bore 152 is the conical head 154 of a pressure valve 156. Valve 146 has a stem 158 received in the wall of housing 120 opposite bore 152 in valve body 144. A coil spring 160 is compressed about stem 158 between housing 120 and head 154 and exerts pressure on head 154 to seat the same in the end of cylindrical bore 152. By threading or unthreading valve body 144 relative to the threads 146 in the interior wall of housing 120, the pressure exerted by spring 158 on conical valve head 154 can be varied to either restrict or enlarge the size of the opening between bore 152 and head 154 and thus the flow of Solution S out of valve body 144 about valve head 154 into chamber 122 during the intake stroke of pump 24.

In operation, upon withdrawal of plunger 128 from cylindrical extension 126, Solution S will enter chamber 122 from valve body 144 against the pressure exerted by valve head 158 against the flow of Solution S through bore 152. By rotating valve body 144, the volume of Solution S per reciprocable stroke of piston 130 entering chamber 122 can be varied due to the relative seating of valve head 158 in bore 152 or the pressure exerted by head 158 against the flow intake of Solution S. Upon the return of plunger 128 in cylindrical extension 126 to complete the pump cycle, the volume of Solution S conveyed into the chamber 122 during the initial phase of the pump cycle is pushed out of chamber outlet port 124, while the flow in chamber 122 maintains sufficient pressure on valve head 158 to maintain the end of bore 152 closed. The volume of flow of Solution S emanating through port 124 per reciprocable stroke of piston 130 also determines the maximum pressure of delivery of Solution S. In this manner, a pulsating jet or stream of Solution S (i.e., on the last half, or return, of the pump cycle) at a controlled flow rate and pressure is delivered through outlet port 124.

Elbow 114 fits over, and can rotate or pivot on, an upright cylindrical extension 162 of housing 120 as shown by the arrows in FIGS. 2 and 5 so that conduit 116 can be aligned with drain conduit 102 in the event of imprecise manufacturing tolerances between cover 52 and box 54 of case 56, or imprecise positioning of the components in container 54. A wire clip 166 (FIG. 2) can be used to aid in holding or clamping elbow 114 to housing extension 162 and an O-ring seal 164 assures a fluid tight joint between the elbow 114 and housing 120.

Figure 7:
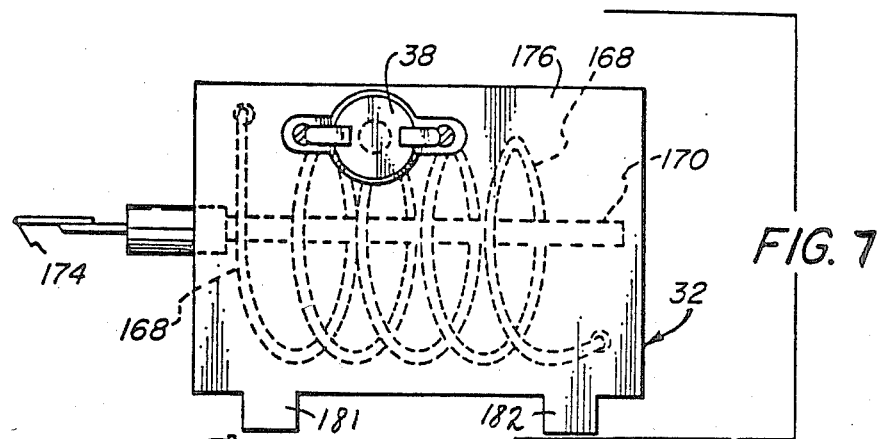
FIG. 7 is a front view in elevation of one embodiment of a heater device for installation in a liquid delivery apparatus in accordance with the present invention.
Figure 8:
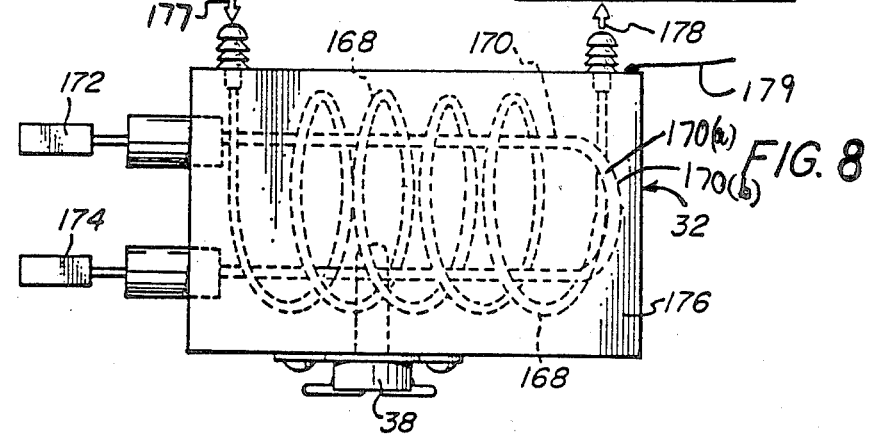
FIG. 8 is a top plan view of the heater device of FIG. 7.
Figure 9:
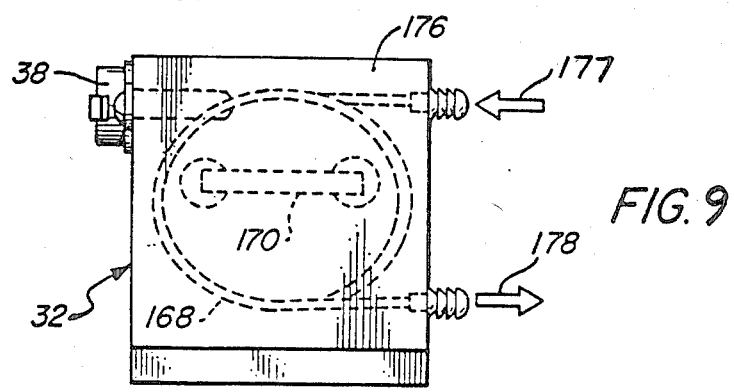
FIG. 9 is a side view in elevation of the heater device of FIG. 8 as seen from the right hand side of FIG. 8.

A quantity of Solution S is delivered through flexible tubing 142 at a controlled rate and pressure to inlet 177 of heating device 32 illustrated in FIGS. 7 to 9. In the embodiment of heater device 32 shown, a conduit comprising a coiled tube, e.g., of stainless steel, is provided surrounding a conventional U-shaped insulated electrical resistance heating element embedded in a heat sink, e.g., a mass of metal advantageously having a high heat capacity. Materials useful for fabricating the heat sink include metals and metal alloys such as aluminum, copper, brass, iron, steel, etc., and non-metals, e.g., various eutectic salt mixtures known in the art. Aluminum serves very well as a heat sink since its high heat capacity endows it with the ability to maintain a relatively constant temperature, e.g., within 5°–10° F. of a predetermined level, depending, of course, on the mass of the metal and the power (thermal) output of the heating element. Aluminum is fairly low in cost and can be readily cast into just about any desired configuration with the heating element and conduit embedded therein.

The liquid to be heated is pumped through the conduit and electrical power is applied to the heating element which transfers its heat to the heat sink. Heat is then transferred from the heat sink to the liquid raising its temperature to a predetermined extent. Such design and operational factors as the heat capacity and mass of the heat sink, the residence time of liquid in the conduit (itself influenced by such factors as fluid pressure and conduit length and diameter), the configuration of the heating element and the power level at which the heating element is operated will determine the temperature to which the liquid is heated. Those skilled in the art can readily establish suitable design parameters for a given service requirement.

A temperature sensor means, e.g., a thermistor, associated with means for controlling the intermittent delivery and interruption of electrical power to the heating element can be secured to the heat sink, preferably near the conduit outlet. The temperature sensor continuously monitors the temperature of the heat sink and, in cooperation with the aforementioned power delivery control means, prevents the temperature of the heat sink from exceeding a predetermined level. This arrangement has several advantages. During steady state operation, i.e., when liquid is flowing through the conduit, the temperature of the liquid at the conduit outlet tends to track the temperature of the heat sink in the vicinity thereof. The temperature sensor emits a control signal which is fed into, and processed by, an electronic circuit of known or conventional design housed at 58 (FIG. 2) which regulates the delivery of power to the heating element. While liquid is flowing, the temperature sensor primarily detects the temperature of the liquid at the outlet. If the liquid flow within the conduit is interrupted, the temperature of the heat sink in the vicinity of the temperature sensor will start to rise because heat is no longer being removed from the heat sink by liquid flowing therethrough. The electronic power control circuit will respond to this increase in temperature by interrupting delivery of power to the heating element if the temperature reaches a predetermined maximum level, e.g., on the order of 105° F. where the liquid being heated is to come into contact with a body. However, the temperature of the stagnant liquid within the conduit will rise by only a modest extent, e.g., approximately 3°-5° F. above the preferred temperature range of about 90°-105° F. Eventually, the temperature of the heat sink, and with it the temperature of the liquid, will begin to drop because of thermal losses. When this occurs, the temperature sensor will signal the power control circuit to resume delivery of electrical power to the heating element. In operation, then, the ability of the heat sink to withstand large fluctuations in temperature permits maintenance of a predetermined temperature level within relatively constant limits, e.g., within 5°-10° F. as may be desired.

When the heater device has not been in operation for a relatively long period of time, the heat sink and any liquid present in the conduit will eventually attain ambient temperature. When the main power switch of the unit is turned on, full heating power is delivered to the heating element to elevate the temperature of the liquid. Placement of the temperature sensor at the outer periphery of the heat sink permits the temperature of the heat sink to rise, e.g., to approximately 105° F., before the power is interrupted by the electronic power controller in response to a signal from the temperature sensor. This elevated temperature persists for a short period, e.g., for approximately five minutes, until thermal losses begin to lower the temperature back to the predetermined level of, say, 98° F.

Referring to FIGS. 7-9, heat sink 176 of heater device 32 is provided as a casting of aluminum metal. Cast block 176 is provided with depending rectangular support legs 181 and 182 for supporting the block on a planar surface. A generally U-shaped electrical resistance heating element 170, e.g., of nichrome wire, and of suitable power rating, e.g., from about 40 to about 120 watts and preferably from about 30 to about 100 watts, surrounded by ceramic electrical insulation 170(a) and encased in a protective sheath 170(b), e.g., of stainless steel, is embedded in the aluminum casting and is provided with external leads 172 and 174 for connecting the heating element to an electrical current source. Heating element 170 can be operated at a constant or varying power level. In the case of the latter, the heating element can be operated for a brief period at the upper end of its rated power range when the unit is first turned on in order to accelerate the heating of cast block 176 and thereafter the power can be reduced to a lower level. A flow of Solution S is introduced into helical, or coiled, conduit 168 at inlet 177 and, heated to the predetermined temperature, is discharged from the conduit at outlet 178. Any suitable means, e.g., a pump, and preferably reciprocating piston-type pump 24, can be used to supply a flow of liquid through conduit 168. Like heating element 170, conduit 168 is embedded in the aluminum casting and is advantageously separated from the heating element by a distance which is sufficient to prevent or minimize the possibility of hot spots developing in Solution S. In operation, heating element 170 will transfer heat to aluminum block 176 which in turn will transfer heat to Solution S present in conduit 168. The temperature of the aluminum block governs the temperature of Solution S, the two being approximately the same.

A temperature sensor 179, e.g., a thermistor, can be mounted on the surface of aluminum block 176 near conduit outlet 178 as part of an arrangement for controlling the intermittent delivery and interruption of electrical power to the heating element whereby the desired predetermined level of temperature is substantially maintained.

In order to maintain Solution S at an optimum temperature, e.g., on the order of about 90° F. to about 105° F., the exterior dimensions of cast aluminum block 176 and the length and diameter of coiled conduit 168 for a given flow rate of Solution S should be suitably selected. If block 176 is too small, it will not possess a sufficient reserve of heat storage capacity to be useful. The maximum amount of heat stored in the block should not exceed its heat capacity for otherwise it will increase in temperature beyond the optimum level desired. If block 168 is too large, it will take too long to heat up to the desired temperature level to be practical. In a preferred embodiment, it has been determined that stainless steel tubing having a minimum length of approximately 48 inches, a minimum internal diameter of about 0.125 inches and wall thickness of approximately 0.02 inches, embedded in an aluminum block whose approximate dimensions are 5 inches×2 inches×2 inches, is sufficient in order to obtain and consistently maintain a predetermined temperature of about 90° F. to about 105° F. in Solution S at a flow rate of 35±5 ml./min. An optimum relationship has been found to exist between the volume of the block/volume of Solution S at a flow rate of 35±5 ml/min once the block has been heated to body temperature in order to attain and maintain proper heating of the solution as it passes through heater device 32. Practical considerations involving economics, time delays in heating and reheating the liquid during intermittent operations, size of the heater, the electrical power input, construction materials of choice, the predetermined temperatures of choice, and the like, will place realistic limits on the dimensions of the components comprising the heater device. Optimization is readily achieved by those skilled in the art.

The flow of Solution S may be interrupted from time to time. However, in certain applications, e.g., in the treatment of teeth with Solution S, since teeth are extremely sensitive to variations in temperature, the solution should still be delivered at a relatively constant temperature regardless of the frequency and duration with which the dentist interrupts the flow of the solution. In the steady state, a continuous input power of approximately 40 watts is usually required to heat Solution S from ambient temperature to a body temperature of approximately 98.6° F. A significant temperature gradient must exist between heating element 170 itself and Solution S passing through heater device 32 in order for sufficient heat energy to be transferred to the solution. At steady state operation, when the solution is being continuously passed through the heater device, electronic controls can regulate the power to the heating element as previously described so that the solution will be discharged at the required temperature. When the dentist releases a switch, e.g., a foot pedal 60 (FIG. 1) or other suitable mechanism, Solution S ceases to flow through the heater. Residual heat energy stored in heating element 170 continues to transfer to casting 176 causing the temperature of the casting, and therefore the solution, to rise only a few degrees above the predetermined temperature of 92°-105° F.

The relationship between the heat capacity of heating element 170 and the heat capacity of aluminum casting 176 which thermally couples conduit 168 containing Solution S to heating element 170, and the heat capacity of Solution S contained in heater device 32 at any given time can be empirically determined. The heater design exploits this relationship to limit the temperature rise during intermittent flow patterns. This ensures both the safety and comfort of the patient. The heat capacity of heating element 170 is limited to a small fraction of the heat capacity of the combined aluminum block 176 and liquid-containing stainless steel conduit 168. This limits the amount of residual heat energy which can transfer to the aluminum casting by the heating element after delivery of electrical power to the latter is interrupted. In a preferred embodiment, the heat capacity of heating element 170 is from about 2 to about 10% of the heat capacity of the remainder of the heater; about 3 to about 5% is highly preferred.

A second temperature sensor 38 is provided as a safety device to prevent the temperature of the aluminum casting from exceeding a predetermined limit should temperature sensor 179 and/or its associated power control circuitry fail to operate properly.

Figure 10:
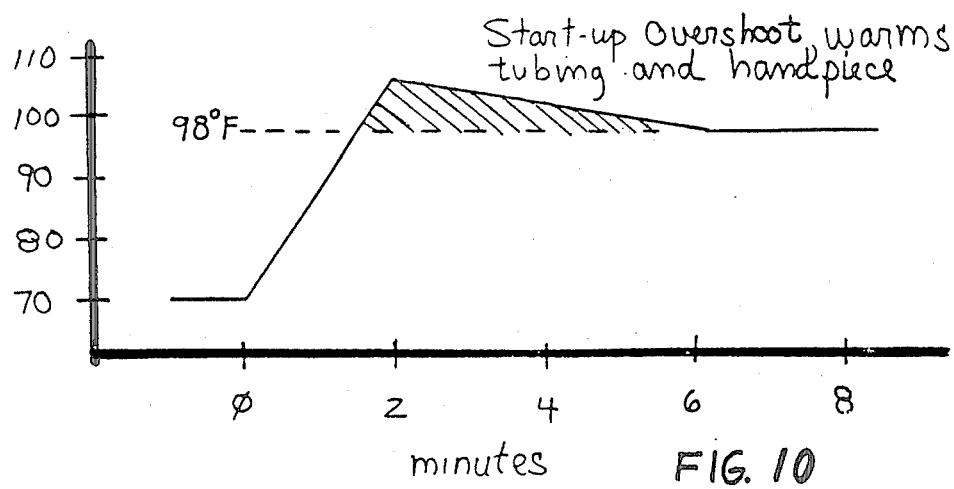
FIG. 10 is a graph illustrating the heating characteristics of the heater device of the present invention after flow of liquid at ambient temperature has been commenced.
Figure 11:
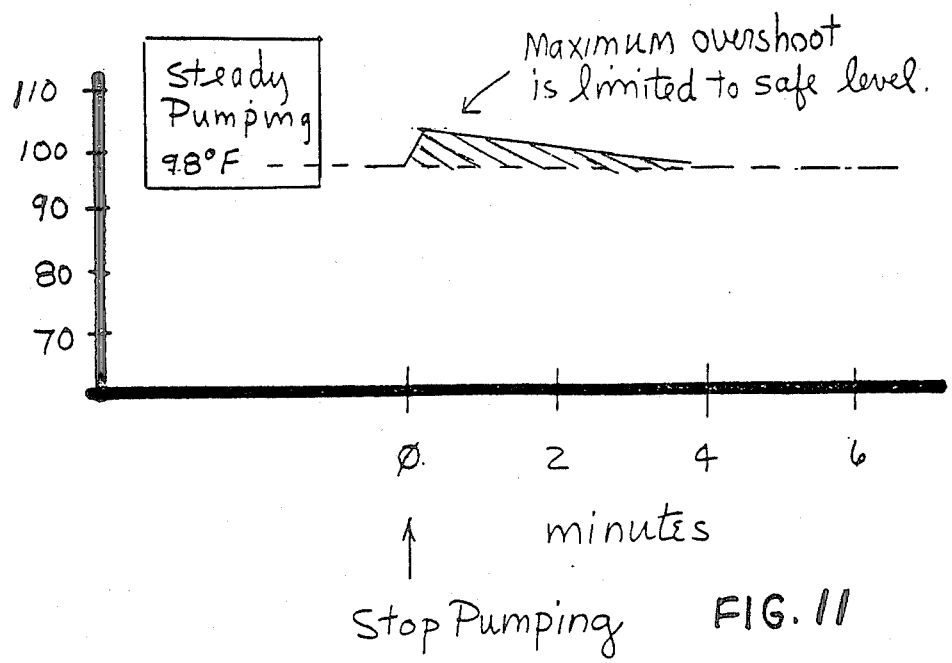
FIG. 11 is a graph illustrating the heating characteristics of the heater device of the present invention after flow of liquid has been interrupted.
Figure 12:
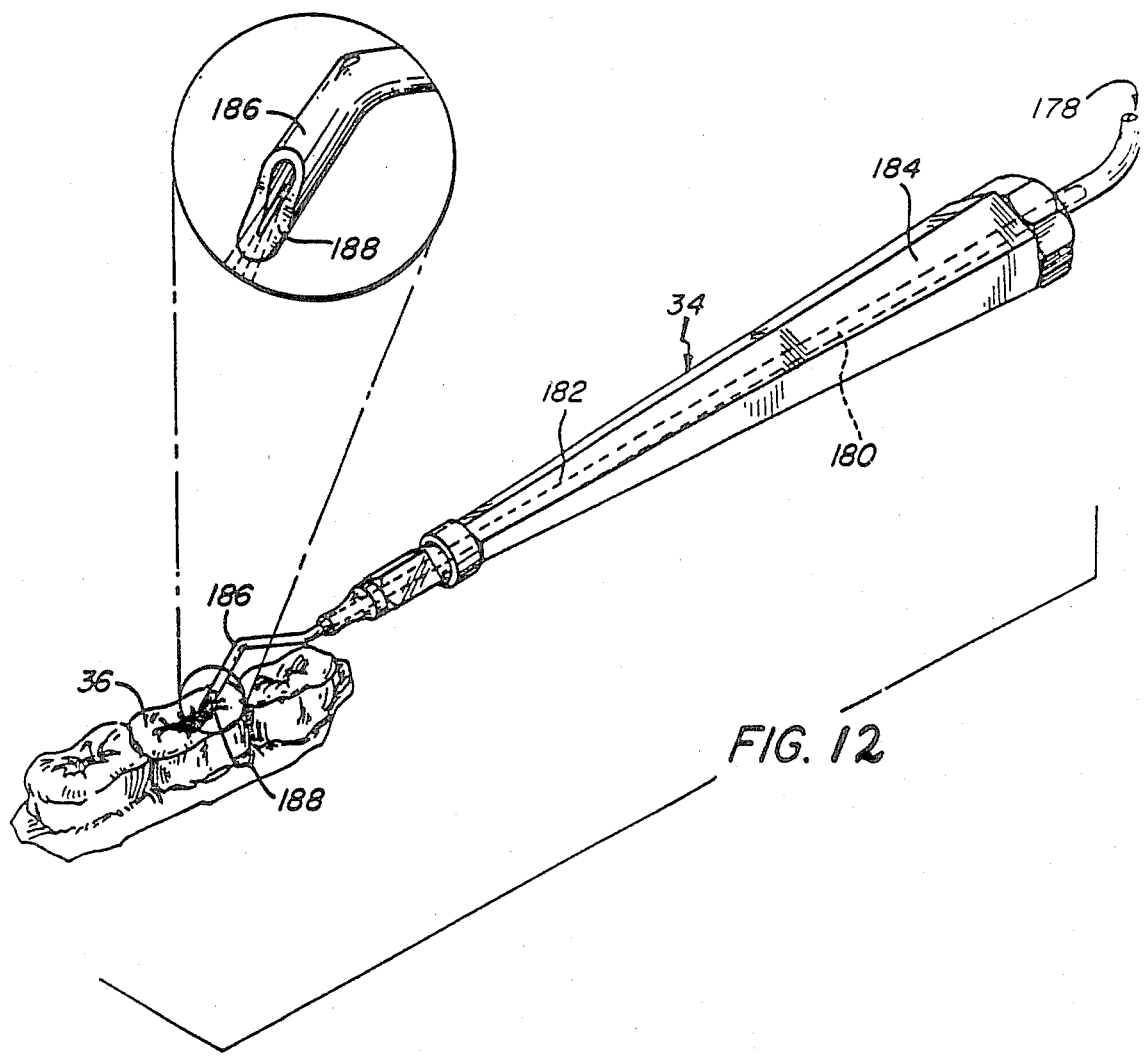
FIG. 12 is a perspective view of the applicator of the apparatus of FIG. 1 with the top portion thereof enlarged in the circled portion of the Figure to illustrate the details thereof; and, FIG. 13 is a diagrammatic block diagram illustrating the overall process of using the heated liquid delivery apparatus of FIGS. 1-12 to deliver a caries/plaque removal solution for treatment of teeth.

As shown in FIG. 10, a typical time/temperature response curve is given for the heater device of FIGS. 7 to 9 where the temperature of Solution S introduced at the conduit inlet is about 70° F. Within about two minutes of start-up employing a heating element output of about 40 watts, there is a brief temperature overshoot which is advantageous in warming the tubing and handpiece of a complete liquid delivery unit used in the treatment of caries as shown in FIG. 12. Within six minutes or so of start-up, the temperature falls back to the predetermined level of 98° F. As shown in FIG. 11, during steady pumping of Solution S, the temperature of the device is uniformly maintained at about 98° F. When the delivery of power to the heating element is temporarily interrupted, there is a modest increase in the temperature of stagnant Solution S present in the conduit (due to the residual heat in the heating element transferring to the aluminum block) which, however, is within an entirely safe level.

As shown in FIG. 12 illustrating applicator 34, flexible tubing 180 runs through the interior of a handpiece 182 having defined lands 184 for easy gripping by a dentist. Tubing 180 is connected to a hollow steel scraping implement 186 having a spoon-shaped tip end 188. Heated Solution S is pumped through tubing 180 into, and through, scraping implement 186 onto the caries/plaque site on tooth 36. Solution S will soften the decay of the caries/plaque and it can then be removed by scraping with spoon-shaped end 188 of implement 186. As Solution S is pumped onto the site, the tip end 188 of implement 186 can also be used to abrade the lesion to aid the solution S in softening the caries material and provide a fresh carious surface on which Solution S can act. Applicator 34 may be supported on a suitable bracket 190 mounted on one end of container 54.

As shown in FIG. 13 which diagrammatically illustrates the use of the foregoing apparatus in the treatment of caries, caries removal Solution S in reservoir 20 is drained through a one-way check valve 22 into a piston-type reciprocating pump 24 provided with flow and pressure regulation means 26 at its inlet and outlet. The piston-type reciprocating pump 24 is driven by an electrical motor 28 which is cooled by a fan 30. Pump 24 causes the pulsating jet stream of Solution S drained from reservoir 20 to flow through a heater device 32 into an applicator device 34 provided with a scraping implement. The applicator 34 directs the solution to the site of the caries at tooth 36.

Heater device 32 maintains the liquid jet stream at from about 90° F. to about 105° F., or optimally at a temperature approximating normal body temperature, so that when it is applied to the site of the tooth caries, it will be neither too hot nor too cold and thus avoid discomfort to the patient. The temperature of heater device 32 is sensed by a thermistor 38 mounted on heater 32 which will cause a signal to be generated should the temperature exceed a predetermined level to stop operation of motor 28 and reciprocation of the piston of pump 24 until the solution cools to approximately to the desired level at which time the motor will once again be started to cause the pump to pump the solution through the heater to the applicator.

Flow and pressure regulator means 26 used in the pump inlet and outlet causes the solution to flow at approximately 35 ml/min at a cycle pressure varying from 10 to 15 psi. This regulation of the flow of the solution as it impinges in the mouth of the patient precludes gum tissue from being ruptured. Such flow and pressure regulation has been found practical via the utilization of a reciprocating piston-type pump wherein suitable flow restrictions can be readily placed at the inlet and outlet during the reciprocatory stroke of the piston to effect flow and pressure regulation.

The applicator causes the chemical solution to be discharged directly at the caries site where it will aid in softening and turning the caries to the extent it can be removed by hand manipulation of the scraper implement associated with the end of applicator 34.

A timer element 40 can be activated upon opening of check valve 22 to drain reservoir 20, and a visual indication, after a given time increment, can be given by lamp 44 as the chemical solution has a very short half life, e.g., on the order of one hour. At that time, the solution in reservoir 20 should be changed to a fresh solution. Operation of the delivery system may be initiated by closing of a manual hand operated switch 59 or a foot-operated pedal switch 60 which will cause operation of pump motor 28 from a pump power source 57. A lamp 62 can indicate that power is on while a lamp 64 can be used to indicate that the system is being operated by foot switch 60.

Heater device 32 is located adjacent to the applicator and scraper and separate from the pump 24 so that: (1) heat loss to the ambient surroundings is minimal after heating of the chemical solution and (2) heating of the chemical solution is independent of any active element in the pump 24 so as to enable effective control of heat imparted to the solution.

What is claimed is:

1. Apparatus for delivering a heated liquid which comprises:

a pump for delivering liquid to a heater device; and, an electrically powered, intermittently operated heater device for heating the liquid discharged from the pump to a predetermined temperature, said heater device comprising:

a heat sink mass;

an electrical resistance heating element embedded within the heat sink mass such that when electrical power is delivered to the heating element, heat is transferred therefrom to the heat sink mass and when the delivery of electrical power to the heating element is temporarily interrupted, residual heat in the heating element is transferred therefrom to the heat sink mass, the total quantity of heat transferred to the heat sink mass from the heating element not exceeding the heat capacity of the heat sink mass so that the temperature of the heat sink mass remains relatively constant both when electrical power is being delivered to the heating element and when the delivery of electrical power to the heating element is temporarily interrupted; and, a conduit for the flow of a liquid to be' heated to a predetermined temperature substantially corresponding to the temperature of the heat sink mass, the conduit having an inlet for admitting liquid at a temperature below the predetermined temperature and an outlet for discharging liquid at the predetermined temperature, the conduit being embedded within the heat sink mass separated a distance therein from the heating element and such that heat is transferred from the heat sink mass to liquid present in the conduit raising the temperature of the liquid from the temperature at the conduit inlet to the predetermined temperature at the conduit outlet.

2. The apparatus of claim 1 in which
   the heat sink mass comprises a block of metal;
   the liquid flow conduit is corrosion-resistant and is embedded within the metal block in the form of a coil and separated such distance from the heating element as to prevent or minimize the possibility of hot spots developing in the liquid,
   the apparatus further including means for regulating the intermittent delivery and interruption of electrical power to the heating element in response to the temperature of the metal block, said means including a thermistor positioned proximate to the conduit outlet to continuously sense the temperature of the metal block; and,
   means for discontinuing the delivery of electrical power to the heating element to prevent the temperature of the metal block from exceeding a predetermined level should said regulating means fail to do this.

3. The apparatus of claim 2 wherein said regulating means is operable to maintain a temperature of liquid at the conduit discharge at or about the normal temperature of a body with which the liquid is to be contacted.

4. The heater apparatus of claim 3 wherein the liquid is a caries/plaque removal solution for introduction into the oral cavity.

5. The apparatus of claim 1 in which the pump is a reciprocating piston-type pump, the apparatus further comprising a reservoir for storing the liquid;

check valve means between the reservoir and the inlet of the pump for establishing communication therebetween when the reservoir is connected to the pump inlet;

flow and pressure regulation means in the outlet of the pump for regulating the flow rate and pressure of the liquid delivered to the heater device; and, applicator means for delivering heated liquid from the heater device for contact to a body or introduction into a body cavity.

6. The apparatus of claim 5 wherein said check valve means comprises:

a pop-up disk seated flush in the bottom wall of the reservoir; and, means connected to the inlet of the pump for raising the disk to allow flow of the solution from the reservoir to the pump upon connecting the reservoir thereto.

7. The apparatus of claim 5 wherein said flow regulation means further comprises:

a hollow valve body disposed in the pump within the hollow interior thereof in communication with the pump inlet, the valve body having an outlet port adjacent the pump outlet; and a spring-biased valve stem having an enlarged head normally closing the outlet port of the hollow valve body;

said valve body being rotatably mounted on said pump such that by rotating same spring bias pressure between the valve stem and the valve body can be varied, to vary the pressure required to move the valve stem relative to the valve body to open the valve body outlet port thereby correspondingly varying the flow rate of solution through the valve body.

* * * * *